United States Patent [19]

Herzstark

[11] 4,268,477
[45] May 19, 1981

[54] APPARATUS FOR DISTRIBUTION OF LIQUID TEST SAMPLES THROUGH VARIOUS TEST STATIONS

[75] Inventor: Curt Herzstark, Vaduz, Liechtenstein

[73] Assignee: BNA-Augustin GmbH & Co. KG, Grafenhausen, Fed. Rep. of Germany

[21] Appl. No.: 48,613

[22] Filed: Jun. 14, 1979

[30] Foreign Application Priority Data

Jun. 15, 1978 [DE] Fed. Rep. of Germany ....... 2826275

[51] Int. Cl.³ ....................... G01N 1/14; G01N 35/06
[52] U.S. Cl. ..................................... 422/64; 141/130; 422/67
[58] Field of Search ...................... 422/64, 63, 65, 66, 422/67; 73/421 R; 364/497; 141/130

[56] References Cited

U.S. PATENT DOCUMENTS

| | | | |
|---|---|---|---|
| 4,039,286 | 8/1977 | Keller et al. | 422/66 X |
| 4,039,288 | 8/1977 | Moran | 422/65 |
| 4,168,955 | 9/1979 | Allington | 422/64 X |

Primary Examiner—Ronald Serwin
Attorney, Agent, or Firm—Frishauf, Holtz, Goodman & Woodward

[57] ABSTRACT

Samples of blood from hundreds of patients are held in test tubes mounted in twenty endless chains of the same number of links, each chain being mounted on a chain-holder keyed so as to be insertable for mounting on only one sector of a rotary disk. A locking member by which the chain is closed must occupy the inside position when the chain is mounted. Since each sample then has a distinctive machine address, program control can then drive the machine so that all the individual samples requiring transfer of a portion for a particular analytical procedure are successively presented to a pipette transfer device, chain by chain, with rotation of all chains so that the chain presented to the pipette apparatus will present in succession only those individual samples requiring the particular analysis samples for the next analytical procedure.

12 Claims, 7 Drawing Figures

APPARATUS FOR DISTRIBUTION OF LIQUID TEST SAMPLES THROUGH VARIOUS TEST STATIONS

This invention concerns apparatus for distribution of liquid samples from a number of sources for various destinations where different types of analysis are respectively performed, as for example the distribution of blood or serum samples taken from a considerable number of patients, for each of whom a number of different tests, not the same in all cases, is to be performed. Although the invention is particularly well suited for use in connection with medical tests of body liquids, it is applicable generally to the handling of liquid samples from a considerable number of individual sources from each of which samples are to be distributed to places where the particular tests requested by or for the source are performed. In the efficient handling of a large number of individual analyses of a variety of types every day, error-proof identification of sample source is a matter of great importance.

Apparatus has already gone into use for facilitating the distribution of samples, for example in laboratories of large clinics, as particularly illustrated in the case of blood tests where samples are taken from the individual patients, resulting in a large quantity of individual samples, which are then collected after being identified in a manner excluding the possibility of confusion or interchange, after which portions of particular size are taken from each of these patient samples as required for the various analytical tests (e.g. determination of blood sugar, cholesterol, and so on) according to the test program prescribed for the particular patient, these portions being put into separate analysis vessels with exact indication of the content and of the analysis procedure to be carried out and then delivered to the appropriate analysis location. The analytical tests carried out where these known distribution installations are provided, such as blood tests for blood sugar, also proceed more or less automatically, which is to say that each of the samples delivered to the clinical laboratory is provided by the physicians with a punched card carrying data regarding the types of tests to be performed, which card is read at the place of distribution and its contents put in a register of a computer system. According to these data, as many portions are taken from each delivered sample at the point of distribution, as there are separate tests to be carried out.

For a possible total count of, for example 45 different analytical tests, 45 rows of analytical vessels would be held ready for filling with sample material at the distribution point. If, for example, the sample taken from a particular patient is to be subjected to analyses no. 3,7 and 28, three portions from the patient would be taken from the patient sample and put into an analysis vessel of each of the rows for tests no. 3, 7 and 28. For the next patient sample, analyses no. 2 and 7 might be required. In that case, portions would be transferred to the respective next vessels of rows number 2 and 7, and so on until all the patient samples, for example 400 in number, are subdivided and put into vessels of the analysis vessel rows.

The above-described procedure takes up a great deal of space and requires a great deal of close attention or, in the case of automatic distribution of the samples, the greatest accuracy, in order to avoid interchanges and other errors in identification, particularly because of the large number of rows of analysis vessels to be made available. This procedure was also quite slow, because the treatment of the filled analysis samples could begin only as soon as the entire quantity of patient samples (in the illustrated example, from 400 patients) could be completely subdivided over all 45 rows of vessels. A preliminary test result for providing a quick overall view was not obtainable in this system. Furthermore, where automatic analysis procedures were used, and the distribution of the samples was not performed over entire rows of analysis vessels before any analysis samples were used, but was carried out in such a way that each of the separate analysis portions would be delivered at once to the automatic analysis station, so that any waiting until the end of the complete distribution was dispensed with, the resulting costs became intolerably high.

Objects of the present invention are to overcome the deficiencies of the previous apparatus and methods, to increase the facility of operating the distribution apparatus, its security and reliability of operation, and also to raise the speed of obtaining analysis results.

SUMMARY OF THE INVENTION

Briefly, at the place of filling, i.e. of transfer of liquid from the patient sample to an analysis sample, only a single row of analysis vessels for a single type of analysis are available at a time and with every feed step of the row of patient sample vessels, only a patient sample needing the above-mentioned single type of analysis will be served by transfer of a portion into the available analysis vessel of the analysis vessel row. The patient samples all bear designations of the work to be done. Thus, only those designating the analysis for which the array of analysis vessels (i.e. a first set of the entire group of patient samples) are destined are served until all the samples for this particular kind of analysis have been obtained from the entire group of patient samples, after which another set of samples in the entire group of patient samples (i.e. those designating another particular kind of test), is brought in sequence to the point of distribution for supply of portions for another particular type of analysis, and so on. The several sets of patient samples selected for the respective analysis designation are usually different, although they ordinarily "overlap" and can occasionally be identical for two different destinations, which is merely to say that the term "set" is used here in its usual technical sense.

The selecting of the relevant patient samples for filling each collection of test vessels is made possible by giving each patient sample a distinctive addressable location on a movable carrier. This is facilitated by using a plurality of indexable endless chains of sample holders. A chain of sample holders of a particular number of members can be readily put in place on a common chain-holder. In order to assure the preservation of the position of each member of the chain and the sample carried by it in the context of the test procedure as a whole, it is useful for each chain of samples to have a distinctive chain-closing member which is required to be placed on the holder at a particular location thereof for emplacement or removal of the carrier on or from a main carrier, while all the other members of the chain carry blocking elements which are fit into a guideway of the holder in which they are movable. Replacement of the holder without the chain-closing member of the chain being in its proper place is thereby mechanically prevented.

BRIEF DESCRIPTION OF THE DRAWINGS

Individual features and details are described and illustrated by way of example with reference to the annexed drawings, in which.

DESCRIPTION OF THE ILLUSTRATED EMBODIMENT

Figure 1:
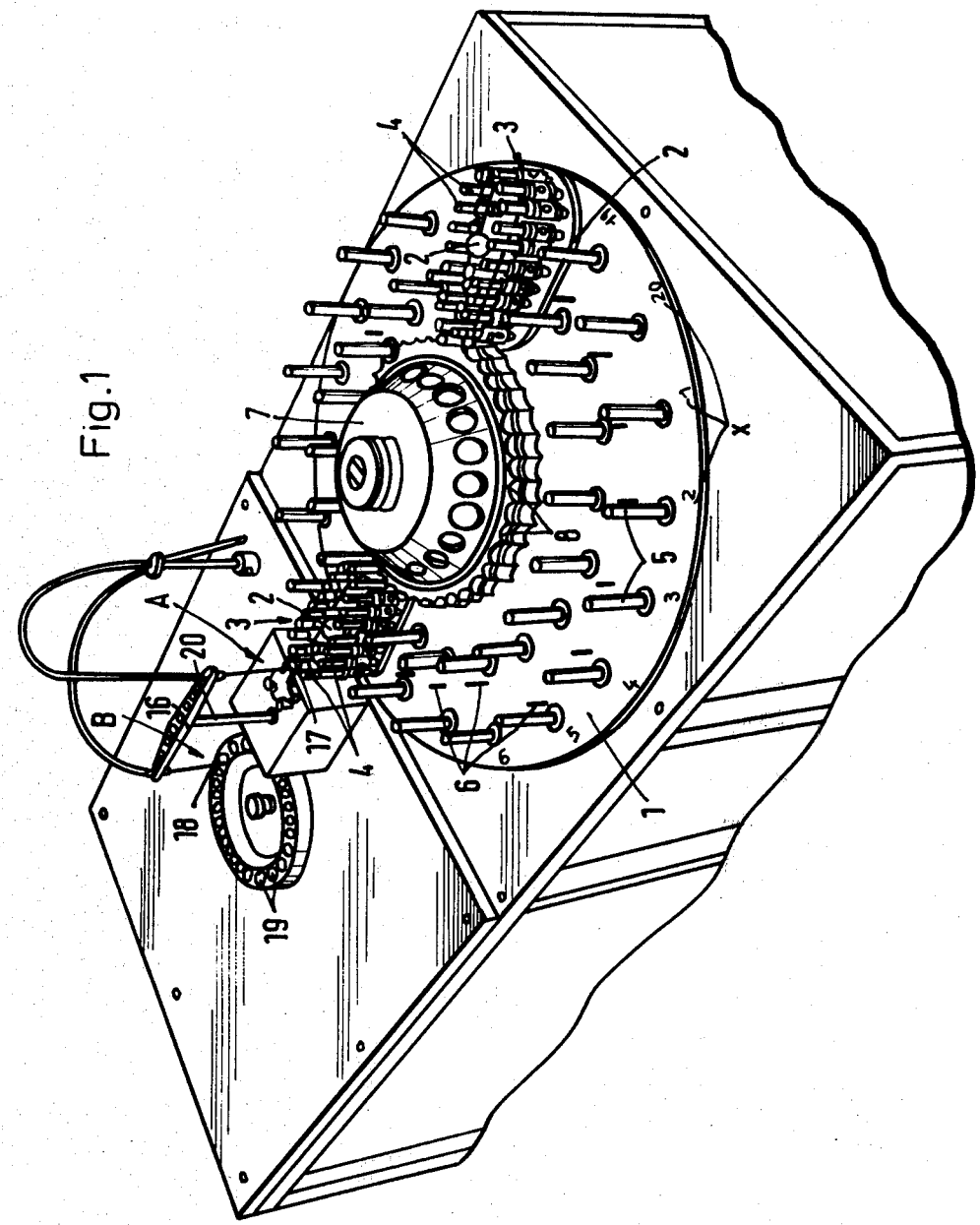
FIG. 1 is a schematic perspective view of an apparatus for distribution of portions of liquid samples for purposes of analysis.
Figure 2:
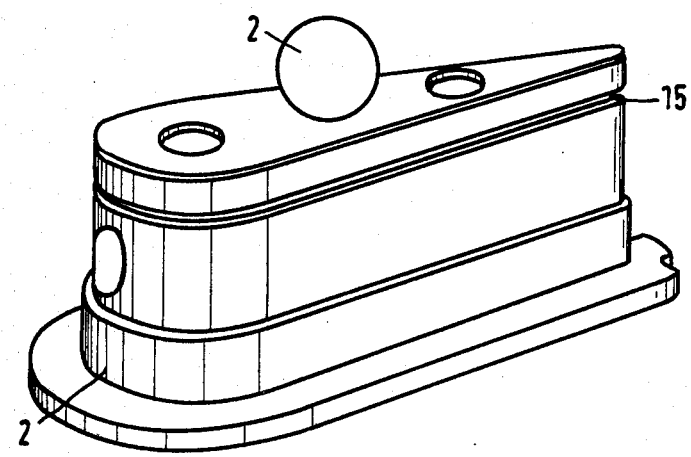
FIG. 2 is a perspective view of an interchangeable holder for chains of sample containers used in the apparatus of FIG. 1.

FIG. 1 shows an embodiment of the invention designed for a daily capacity of 400 patient samples for blood tests. Twenty removable holders 2 are provided on a disk 1 which is rotatable about a vertical axis. On each of the holders 2, a closed chain 3 of twenty patient sample vessels 4 can be inserted, each sample vessel being illustrated as a test tube of, for example, 5 ccm capacity, so that altogether 400 of such test tubes are available for drawing off one or more portions. Of these holders 2 bearing chains 3, only two are shown in the drawing. Each of these chain-holders 2 bears on its underside, in addition to the holding and guiding holes for the pins 5 with which the rotary disk 1 is equipped, also identification holes into which corresponding identifying pins 6 of the carrier disk 1 engage.

The twenty chain-holder locations are designated with the numbers 1 to 20, as illustrated for a few cases at 25. Each identifying pin 6 corresponds to a correspondingly disposed hole on the underside of the chain-holder, so that each individual holder is assured to be found in one and the same location permanently assigned to it whenever the particular holder is on the disk 1.

The use of a flat carrier disk or plate, as shown, makes possible preservation of the blood samples taken daily from many patients, at 4 Celsius in the usual type of container, without occupying an undue volume of space.

The disk 1 is rotatable in either direction of rotation by any of certain angles (portions of a revolution) by a drive 7 which is program controlled. These angles are either the angle between the centers of two neighboring chain-holders 2 whey they are in position on the rotary disk (this angle being 18° in the illustrated example of twenty holes), or some integral multiple of that angle.

Similarly, the chains 3 of holders for the several patient sample vessels carried on the several chain-holders 2 mounted on the disk 4 can be driven, as illustrated, by a central spur gear or star wheel 8, in either direction of revolution of a chain around its holder 2, likewise under program control. With monitoring by program-controlled driving means, the revolution of the carrier disk 1 and, independently thereof, also the displacement of the sample vessel chains 3, can be produced either slowly, or by means of a fast drive, in steps of different sizes, so that much time can be saved by skipping over sample containers from which no transfer is to be made at the particular time.

Figure 5:
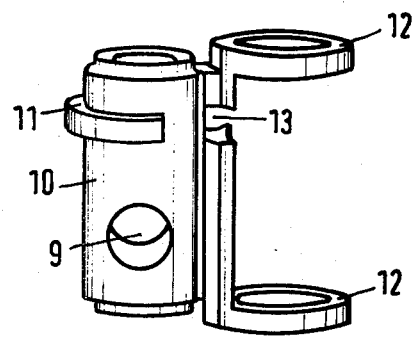
Figure 6:
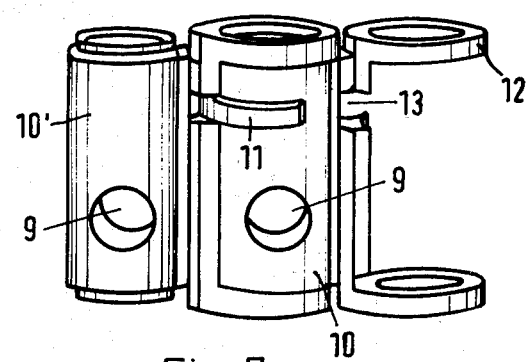
Figure 7:
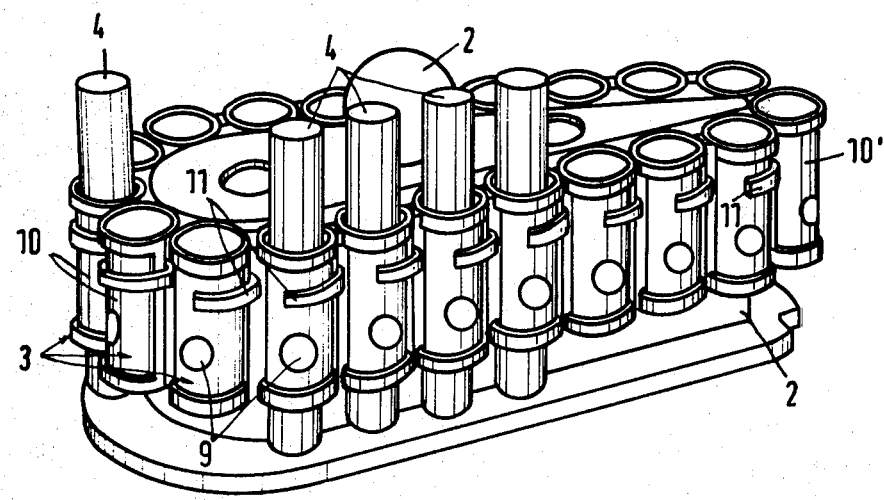
FIG. 7 is a perspective view illustrating the placement of patient sample vessels in the sample holders of a chain, while the latter is mounted on a chain-holder, in this case located away from the distribution apparatus as a whole.

The permanently connected sample-holding-chain 3, which in the illustrated example is stretched around and on the holder 2, consists of members that fit together in articulated fashion, as shown in FIGS. 5-7. Each member has a tubular pocket 10 in which a sample vessel 4 of test tube shape is insertable. As illustrated in the drawings, it is convenient to provide each member with a window 9 for purposes of such observation or checking as may sometimes need to be made without removal of the sample. These pockets 10 (with the single exception of the pocket 10') carry a circumferential ridge or rib 11 on a part of their circumference and, on the opposite side, two holding rings 12 in which one of the neighboring pockets 10 is free to revolve. At the level of the outer ridge or rib 11, the mounting yoke of the rings 12 has an incision 13 into which the rib or ridge 11 of the neighboring pocket extends. The chain-holder 2 has a circumferential groove 15 which is at least as wide as the ridges 11, in which they move.

Figure 4:
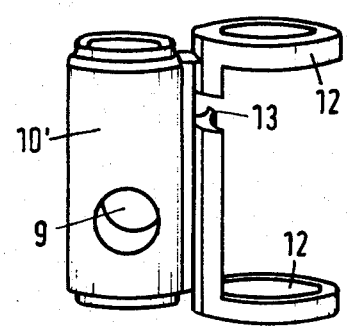
FIGS. 4-6 are representations of a few members of the chain of individual sample holders in various attitudes, FIGS. 4 and 6 showing the chain-closing members.

As already mentioned above, a single closing member 10', which is a member without a ridge 11, is provided in the articulated chain, this being particularly shown in FIG. 4. Until this closing member 10' is put in place, a chain which is still open (which is to say, without this closing member) can easily be placed around the chain-holder 2, in which operation the ridges 11 fit into the groove 15.

Figure 3:
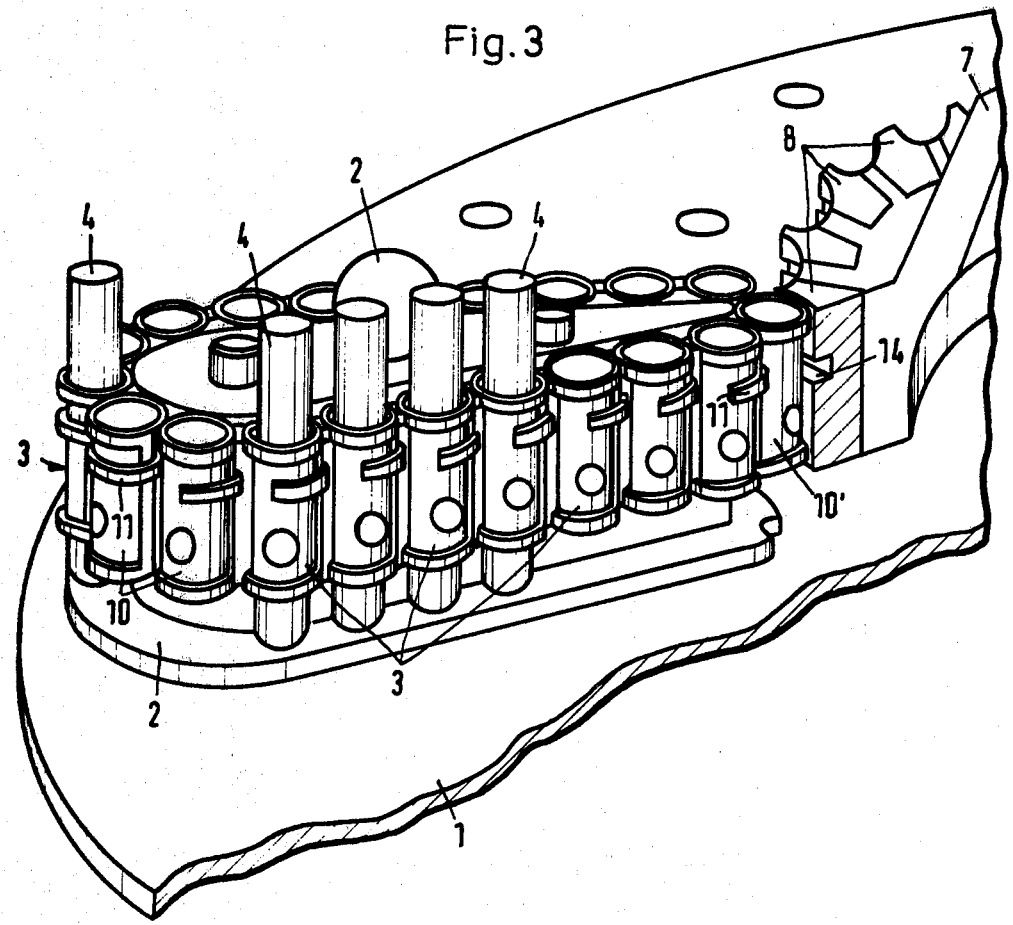
FIG. 3 is a perspective view, partly cut away in section, of a holder of the kind of FIG. 2, loaded with a chain of individual sample holders, and of the central drive of this chain.

As shown in FIG. 3, the teeth of the gear 8 are provided with an incision or notch 14. These notches 14 and the groove 15 serve to guide the chain members by their ridges 11 during their displacement by the gear 8. In order that these ridges do not interfere with the insertion of the holder 2 with its fully connected chain into the operating machinery of the apparatus, it is provided that the member 10' is without a guide ridge and that it must always be on the portion of the holder facing inwards of the disk when it is mounted on the disk. If then the chain is not exactly in this position on the holder, the holder cannot be set in place and likewise cannot be taken out, because a guide ridge 11 fitting into a notch 14 would block such an operation. This missing guide ridge on the one of the twenty chain members does not at all, however, hinder the displacement and pulling around of the chain. The test tubes 4 inserted in the pockets 10 also tend to provide supplementary assurance that the chain members will be held together.

Just as the closing of the sample rows into respective endless chains 3 is useful for addressing any one of the patient samples by a combination of motions, a similar use of closed chains can also be used at the location of the analysis vessels, for example for various analysis chains into the vessels of which may be transferred the sample portions selected by the above-described distribution apparatus. In each instance, this chain arrangement provides increased reliability of addressing the sample store, as well as better manual accessibility to any desired sample.

The transfer of liquid from patient sample vessel to analysis sample vessel is carried out by an automatic pipetting apparatus delivering into smaller analysis vessels of, for example 1.5 ccm content. Of that content, 0.5 ccm is for the volume of the sample itself, and the ramainder of the vessel capacity is for the reagents to be used in analysis.

The transfer pipettes are affixed to the arms of a horizontal beam 16. One arm of this beam carries the vertical withdrawal pipette 17 for suction of the sample portion from the patient sample vessel 4, which is operated under program control by means not illustrated. The other arm of the beam carries a vertical pipette 18 that, at the place of delivery, spills out into one of the analysis vessels 19 of a row or chain of such vessels, in each operation, the sample sucked up in the previous dwell-step of the machine from one of the patient sample vessels 4. A vertical shaft 20 that carries the beam 16 swings back and forth for these operations and is concurrently also moved up and down. These movements are performed under control and monitoring, by the same electronic control system that controls the disk 1 and the gear 8, according to a previously provided operation program. Electronic control systems for producing movements in accordance with a prescribed program, particularly for movements in accordance with a prescribed program, particularly for movements as simple as those herein described, are very well known and since they form, as such, no part of the present invention, they therefore do not need to be further described here. These systems are preferred in modern practice, for reasons of economy and flexibility, over the earlier techniques utilizing cam controlled mechanical movements and the like.

It will be evident that the illustrated embodiment can be modified or varied in many ways within the scope of the inventive concept here disclosed. For example, the holders 2 with analysis sample holding chains 3,4 can be replaced by rotary disks or flat-faced or otherwise shaped carrier bodies movable on the disk 1 and provided with holes for receiving the sample portion vessels.

Before the drive of the disk 1, the gear 8 and the shaft 20 are set in motion, every individual sample vessel 4 has a fully defined position in the machine. This is reliably assured by the fact that each chain-holder 2 can be put in position only in a fully defined sector of the disk 1 (which the identifying pins 6 serve to define) and, further, by the fact that each chain 3 initially takes the position on its chain-holder 2 in which the ridgeless member 10' is in engagement with the gear 8. Therefore, the initial position of each individual sample portion vessels 4 can be registered in machine-readable form, for example on a punched card. Under control of this registration, the driving apparatus, is then caused to operate the drives of the above-mentioned components 1, 8 and 20, so as to present the sample portion vessels 4 to the pipette 17 in a definite programmed sequence by the shortest path.

I claim:

1. Apparatus for distribution of portions of many samples of liquids, obtained from different sources, to a plurality of destinations according to a set of destinations individually prescribed for each sample, so that a set of said samples is identifiable for each of said destinations for delivery of a sample portion to the particular destination, comprising:

means for mounting each of a multiplicity of said samples of liquids, each in an individual vessel, in a distinctive and addressable position on a first movable carrier (1);

means for actuating said first carrier controllably so as to present any predetermined set of said samples selected from among all the samples on said carrier, in succession, to a liquid transfer station at a fixed location alongside said carrier, with a period of dwell at said station to permit liquid transfer at each presentation of a sample to said station, and to do so substantially without intermediate stopping of said first carrier between said dwell periods and without intermediate presentation to said station of any sample not belonging to said predetermined selected set;

means for transferring a portion of each liquid sample of said set, while said samples are respectively presented by said first carrier at said station, into an individually identified container of a set of containers having a common destination and held on a second carrier for transfer to said destination; and means for causing said actuation means, after the actuation of said first carrier thereby for presentation of a first set of samples to said liquid transfer station for transfer of sample portions to containers having a first common destination, to execute the presentation of a second set of said samples on said first carrier, possibly but not necessarily different from said first set, to said liquid transfer station for transfer of sample portions to containers having a second common destination and held on a third carrier for transfer to said second destination, and so on, until containers for all waiting destinations have been supplied with prescribed sample portions, whereby the respective sets of containers for said destinations are ready for removal to said destinations in sequence, while time is saved by omission of nugatory presentations of samples to said transfer station, and reliable preservation of sample identity is also provided.

2. Apparatus as defined in claim 1, in which said transferring means comprises an automatic pipetting device (16–20) arranged to be driven in coordination with said actuating means during the dwell periods of said actuating means for transfer of a portion of predetermined volume of each of said samples which is presented to said liquid transfer station, into one of said individually identified containers.

3. Apparatus as defined in claim 2, in which said first carrier comprises a disk (1) rotatable about a vertical axis having seating places for a multiplicity of detachable and replaceable chain-holders (2), each shaped for holding a multiplicity of vessels (4) in a closed chain, while permitting movement of said chain and vessels (4) around the chain-holder (2) for displacement of liquid samples contained in said vessels (4), and in which said actuating means includes a member for engaging the chains carried on the chain-holders seated on said disk for displacement of said sample-containing vessels (4) on said carrier.

4. Apparatus as defined in claim 3, in which each of said chains (3) has a single vessel-holding member (10') having a shape which requires it to be in a predetermined position upon one of said chain-holders (2) when that chain-holder is seated on or removed from said disk (1).

5. Apparatus as defined in claim 3, in which said member of said actuating means for producing displacement of said chains on said holders is in the form of a driving spur wheel (8) centered on said axis of said disk (1) and having a number of drive teeth corresponding to the number of chain-holders (2) that can be seated on said disk.

6. Apparatus as defined in claim 2, in which said pipetting device (16–20) comprises a cross beam (16) mounted on a vertical rotary shaft (20) for swinging about a vertical axis and carrying on its opposite ends pipettes (17,18) connected and equipped for intermittent liquid transfer, of which one pipette is arranged to cause sucking up of a liquid contained in a sample-containing vessel (4) presented to said liquid transfer station, and the other pipette is arranged to dispense a previously sucked up sample portion into one of said individually identified containers (19) then lying beneath it, whereby each of said pipettes (17,18) alternately performs the functions of sucking up a sample portion and dispensing a sample portion in successive dwell periods of said actuating means.

7. Apparatus as defined in claim 5, in which said member (8) of said actuating means for displacing said chains (3) and a portion of said actuating means for displacing said disk (1) are independently controllably actuatable between said dwell periods of said actuating means.

8. Apparatus as defined in any of claims 1,4,5 and 7, in which said disk and said chain-holders are keyed by interfitting shaped members in such a way that any one of said holders can be effectively seated only in a predetermined sector of said disk.

9. A modular-turret sample-sorting carrier for holding a multiplicity of liquid sample vessels in randomly addressable array for selectable presentation at at least one fixed-location station, comprising:

a rotatable disc-like table having a plurality of seating positions in successive sectors of said table for radially disposed elongated island-like detachable hubs of multiple sample-vessel holding aggregates;

a set of multiple-vessel holding aggregates, one for each of said sectors of said table, each aggregate including a circumferentially smooth central hub detachable from said table and a multiplicity of vessel-holding members each having an upwardly open cavity for seating one of said vessels, and means for linking said members in a closed chain around the hub, said vessel-holding members being separable from each other and, with said linking means, also separable from the hub; and driving means located at least partly in said table and including a spur device engageable with closed chains of said members when the latter are established around their respective hubs, for moving said chains around said hubs and controllably presenting any selected member of a chain at the chain position that is radially outermost with respect to said disk.

10. A modular-turret carrier as defined in claim 9, in which each said hub forms part of a holder for the remainder of the vessel-holding aggregate and has a surface upon which the bottom portion of said vessel-holding members may slide, said hub of each aggregate being of a size for holding a chain consisting of a predetermined number of said vessel-seating members.

11. A modular-turret carrier as defined in claim 10, in which all but one of the respective combinations of a vessel-seating member and the portion of the linking means surrounding said member include a blocking piece (11), and in which said hub is provided with a circumferential groove into which said blocking piece (11) of said members fit, whereby said combination of hub holder and chain is caused to be fittable into one of said seating positions of said table only when that one of said members (10') which has no said blocking piece occupies a predetermined position on said hub.

12. A modular-turret carrier as defined in claim 9, in which each of said vessel-seating members has a bore providing an observation path through said cavity for observation of the contents of a vessel held in said cavity to facilitate checking the identity of said vessel by suitably placed markings on said vessel, particularly upon insertion, removal and replacement of a vessel in said cavity.

* * * * *